(12) United States Patent
Tatebayashi et al.

(10) Patent No.: US 7,190,992 B2
(45) Date of Patent: Mar. 13, 2007

(54) MAGNETIC RESONANCE IMAGING USING TECHNIQUE OF POSITIONING MULTI-SLABS TO BE IMAGED

(75) Inventors: Isao Tatebayashi, Utsunomiya (JP); Naoyuki Takabayashi, Otawara (JP); Naoyuki Furudate, Otawara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 439 days.

(21) Appl. No.: 10/231,443

(22) Filed: Aug. 30, 2002

(65) Prior Publication Data
US 2003/0139660 A1 Jul. 24, 2003

(30) Foreign Application Priority Data

| | | | |
|---|---|---|---|
| Jan. 18, 2002 | (JP) | | 2002-010249 |
| Apr. 2, 2002 | (JP) | | 2002-099508 |
| Apr. 3, 2002 | (JP) | | 2002-101045 |

(51) Int. Cl.
*A61B 5/055* (2006.01)
(52) U.S. Cl. ...................... 600/410; 324/309
(58) Field of Classification Search ................ 600/410; 324/307, 309
See application file for complete search history.

(56) References Cited

U.S. PATENT DOCUMENTS

| | | | | | |
|---|---|---|---|---|---|
| 4,665,367 | A | * | 5/1987 | Kramer et al. | 324/309 |
| 4,920,573 | A | * | 4/1990 | Rhodes et al. | 382/131 |
| 5,365,927 | A | * | 11/1994 | Roemer et al. | 600/410 |
| 5,512,827 | A | * | 4/1996 | Hardy et al. | 600/410 |
| 5,537,039 | A | * | 7/1996 | Le Roux et al. | 324/309 |
| 5,617,521 | A | * | 4/1997 | Goto | 345/426 |
| 5,631,560 | A | * | 5/1997 | Machida | 324/309 |
| 5,699,799 | A | * | 12/1997 | Xu et al. | 600/407 |
| 5,719,498 | A | * | 2/1998 | Hausmann | 324/309 |
| 5,825,908 | A | * | 10/1998 | Pieper et al. | 382/131 |
| 5,877,760 | A | * | 3/1999 | Onda et al. | 715/784 |
| 5,883,933 | A | * | 3/1999 | Goto et al. | 378/62 |
| 6,157,194 | A | * | 12/2000 | Vassallo et al. | 324/322 |
| 6,215,305 | B1 | * | 4/2001 | Haselhoff et al. | 324/309 |
| 6,275,035 | B1 | * | 8/2001 | Debbins et al. | 324/307 |
| 6,331,776 | B1 | * | 12/2001 | Debbins et al. | 324/309 |

FOREIGN PATENT DOCUMENTS

| | | |
|---|---|---|
| JP | 01-254149 | 10/1989 |
| JP | 06-022933 | 2/1994 |
| JP | 08-289888 | 11/1996 |

* cited by examiner

*Primary Examiner*—Ruth S. Smith
(74) *Attorney, Agent, or Firm*—Nixon & Vanderhye P.C.

(57) ABSTRACT

A magnetic resonance imaging system is provided for obtaining MR images by scanning a region of the object previously located on an object's positioning image. The system comprises a displaying unit, inputting unit, approximating unit, and locating unit. The displaying unit displays a plurality of tomographic images of the object as the positioning image, each of the tomographic images including an indication of a target of interest thereon. The inputting unit enables information about a running state of the target in a direction along the target to be supplied toward each of the tomographic images. The approximating unit calculates three-dimensionally an approximated curve indicating the running state of the target in the direction on the basis of the supplied information about the running state. The locating unit locates the region substantially perpendicular to the approximated curve.

19 Claims, 16 Drawing Sheets

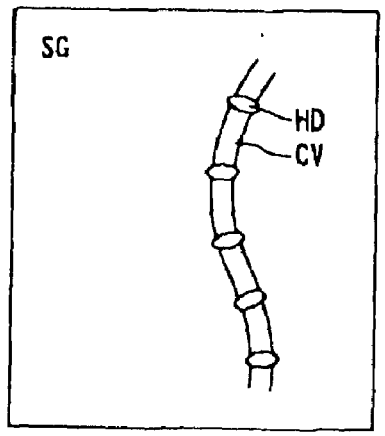 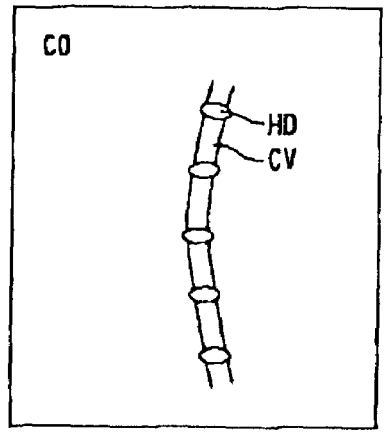
FIG. 4A  FIG. 4B
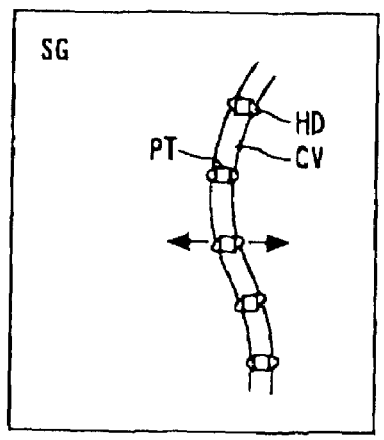 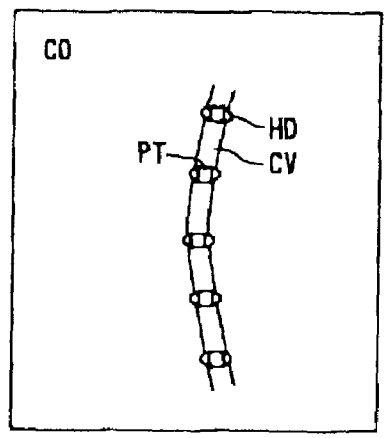
FIG. 5A  FIG. 5B

MAGNETIC RESONANCE IMAGING USING TECHNIQUE OF POSITIONING MULTI-SLABS TO BE IMAGED

BACKGROUND OF THE INVENTION

1. Technical Field of the Invention

The present invention relates to magnetic resonance imaging for an object, and in particular, to both of the magnetic resonance imaging with a highly improved positioning technique for multi-slabs to be located at the positions of object's targets, such as a vertebral column, and an easy-to-use interface for the positioning technique.

2. Related Art

Magnetic resonance imaging (MRI) is generalized as a technique based on the behavior of nuclear spins of an object positioned in a static magnetic field. A radio frequency (RF) signal of a Larmor frequency is applied to the object in order to realize magnetic excitement of the object. MR signals are induced and acquired responsively to the excitement, and subjected to reconstruction processing of MR images of the object.

This magnetic resonance imaging is also suitable for imaging of vertebral columns, such as a cervical vertebra, dorsal vertebra and lumbar vertebra. This is because the magnetic resonance imaging allows an object's scanning section to be set at any angle and provides cartilages and others with a higher contrast than that provided by other imaging modalities. Normally, an imaging technique called a multi-slab scan is used for such vertebral columns, providing a plurality of MR images of intervertebral disks.

For example, for diagnosing herniated disks using a magnetic resonance imaging system, a section along the intervertebral disks is scanned based on, normally, a multi-angle and multi-scan technique combined with the multi-slab scan. For this imaging, it is required to plan a scan to determine the positions of slices on a positioning image, which is for instance a sagittal image of the intervertebral disks.

In normal diagnosis, a plurality of slices are located at one or more desired disks in a mutually adjacent and parallel manner in order to examine how deep the hernia develops in the column direction. Such adjacent and parallel plural slices are called a slab. Hence a plurality of slabs are located on the positioning image at arbitrary positions and angles independently of each other. Hence the slabs can be located at different positions at different angles. The determined slabs are then subjected to scanning carried out at a time based on the multi-angle and multi-scan technique.

How to plan an imaging scan, including how to locate slices, which is suitable for imaging the vertebral column of a human body (i.e., an object) is exemplified by for instance Japanese Patent Laid-open Publication Nos. 1994-22933 and 1996-289888.

The former publication discloses, as one aspect, a technique of planning a scan for MR imaging. To be specific, with viewing a sagittal image of a lumbar vertebra, an operator initially positions a slice in parallel with a desired intervertebral disk on the image. Responsively to this positioning operation, a calculator operates according to a series of previously stored procedures so that a single initial slice is placed at a position and an angle, as specified. The calculator automatically places one or more adjacent slices on an upper or lower side of the initial slice.

Referring to FIG. 1, a more practical way of setting a plurality of slabs according to the teaching from the above former publication, which is carried out interactively with an operator, is as follows.

(1) At a predetermined default position on a sagittal image, a first slice is displayed;

(2) a mouse is used to adjust the first slice in its position, thickness, length, angle, and others;

(3) the number of slices to be placed adjacently to in parallel with the first slice is given, thus producing plural slices, thus producing a first slab SL1;

(4) like the above, a second slice is displayed at a desired disk location;

(5) a mouse is used to adjust the second slice in its position, thickness, length, angle, and others; and (6) the number of slices to be placed adjacently to in parallel with the second slice is given, thus producing plural slices, thus producing a second slab SL2.

Through these operations, as exemplified in FIG. 1, the first slab SL1 consisting of three slices and the second slab SL2 consisting of two slices are designated.

Meanwhile, of the foregoing publications, the latter discloses a technique of planing imaging carried out by an X-ray tomographic radiographing apparatus. Such a technique can also be performed by a magnetic resonance imaging system. Practically, an auxiliary image (X-ray spectroscopic image) acquired around a vertebral column is used to recognize each intervertebral disk, and then specify a middle position in a plane between intervertebral disks to determine a scan position. Further, from the auxiliary image, a centerline that passes through the vertebral column is drawn to detect a scan angle as being perpendicular to the centerline. The thus-detected scan position and scan angle are incorporated in the planning data.

Normally, the vertebral column in the human body is curved three-dimensionally, so that planes positioned in parallel with the intervertebral disks are directed in various ways, respectively. The conventional scan plan techniques use a single two-dimensional image, as described by the foregoing publications. Thus it was very difficult that each slice to be imaged was almost completely in accord with each intervertebral disk.

When taking these conditions into account, to precisely determine the directions of slices in parallel with individual intervertebral disks tilted three-dimensionally may result in a second technique of using a plurality of images to determine a scan position and a scan direction. The use of the plurality of two-dimensional images means that a scan plan is established on each of the images. A period of time required for the planning is therefore made longer remarkably, thus making the total imaging time longer as well. Adopting the second technique is not practical.

Even for the same vertebral column, degrees of diagnostic interest are dependent on individual intervertebral disks. It is desired that the number of slices assigned to each intervertebral disk be therefore freely changeable every intervertebral disk, according to an upper limit of the number of slices, which results from a pulse sequence to be used, and degrees of medical interest. However, it was difficult to accurately change the number of slices every intervertebral disk on each two-dimensional image. In addition, using a plurality of two-dimensional images for changing the number of slices was also almost impossible when considering a time limit.

Moreover, the foregoing technique for positioning slices (slabs) causes an inconvenience when an operator desires to change or adjust contents of the parameters of the slabs that have been determined once. Such cases happen when the number of slices incorporated in a slab is desired to be changed or sizes (e.g., width and/or length) of a slice are desired to be changed. If assuming that changes in the number of slices composing a slab is desired, the following operations will be carried out interactively with an operator:

(1) a mouse is used to move a cursor to a desired slab on a positioning image for selection thereof;

(2) the mouse is again used to move the cursor to a window in which the number of slices are inputted, the window being positioned outside the positioning image, and to select the window; and (3) a keyboard is used to input a desired numeric value for the number of slices.

As understood from the above, it is required for an operator that both the mouse and the keyboard be used to change values of any parameters of slices (such as the number of slices, sizes of a slice, or others). Using both tools is thus very burdensome for the operator. In addition, whatever the operator wants to change parameters of a slice, the operator should move the cursor between the positioning image and the parameter-changing window, thus amplifying the burdensome operations.

Differently from setting slices to be scanned, a further region to suppress influence resulting from blood flow and others, called a saturation region, should frequently be determined on a positioning image. If one or more saturation regions are determined, an RF saturation pulse is previously applied to the saturation regions, so that signals acquired from the regions are suppressed.

In cases where setting such saturation regions is desired, a saturation region of an arbitrary angle and size is placed at a default position on a positioning image in the similar manner to that for slices. Then a mouse is used to click part of the initial saturation region to move and/or rotate it, thereby being adjusted into a final saturation region of a suitable angle and size.

However, when the number of saturation regions increases, the operational work becomes heavy in proportional to the number of saturation regions and a time required for the setting work is made longer, reducing efficiency thereof.

SUMMARY OF THE INVENTION

The present invention has attempted to break through the foregoing current situations. A first object of the present invention is to provide both of a magnetic resonance imaging system and a magnetic resonance imaging method, which are able to have a planning function for imaging, which allows imaging slices to be located at desired positions of an object more precisely and quickly, even if the object is three-dimensionally curved, like a vertebral column such as a lumbar vertebra.

A second object of the present invention is to provide both of a magnetic resonance imaging system and a magnetic resonance imaging method, which are able to have a function of freely changing the number of imaging slices every intervertebral disk, depending on degrees of clinical interest, in addition to the foregoing first object.

A third object of the present invention is to provide an interface equipped with a magnetic resonance imaging system, which allows an operator to smoothly change values of parameters, or conditions, of slices with extremely lightened burdens imposed on an operator.

A fourth object of the present invention is to provide an interface equipped with a magnetic resonance imaging system, which allows an operator to improve efficiency of setting saturation regions, if the number of saturation regions to be set on a positioning image is increased.

As one aspect of the present invention, there is provided a magnetic resonance imaging system for obtaining an MR image of an object by scanning a region of the object previously located on a positioning image previously acquired from the object. The system comprises a displaying unit, inputting unit, approximating unit, and locating unit. The displaying unit displays a plurality of tomographic images of the object as the positioning image, each of the tomographic images including an indication of a target of interest thereon. The inputting unit enables information about a running state of the target in a direction along the target to be supplied toward each of the tomographic images. The approximating unit calculates three-dimensionally an approximated curve indicating the running state of the target in the direction on the basis of the supplied information about the running state. And the locating unit locates the region substantially perpendicular to the approximated curve. The gist of this configuration is also adapted to a magnetic resonance imaging method as included in the present invention.

Accordingly, even if a target (e.g., lumbar vertebra) to be diagnosed is curved three-dimensionally within an object, the locating unit locates a scanning region (e.g., a plurality of slabs each consisting of one or more slices) perpendicularly to the target in the running direction thereof in a more precise and speedy manner. In addition, depending on degrees of medical interest, the scanning regions can be freely changed or increased in number.

By way of example, the tomographic images serving as the positioning image is two in number and the region is one or more slabs each consisting of one or more slices. Preferably, the two tomographic images (for example, sagittal and coronal images of a vertebral column such as a lumbar vertebra) are substantially perpendicular to each other.

It is preferred that the inputting unit is configured to allow an operator to specify a plurality of desired points, which indicates the running state information, along the target on one of the two topographic images. In that case, the approximating unit projects the desired points specified on the one tomographic image onto the remaining tomographic image, and allows the operator to move the projected points on the remaining tomographic image. The approximating unit further calculates an approximated curve passing three-dimensional crossed points at which the points on each of the two tomographic images are crossed with each other. The locating unit allows the operator to select a desired position along the approximated curve, and locates the slab at the desired position of the approximated curve so that the slab is substantially perpendicular to the approximated curve.

Still preferably, the locating unit allows the operator to specify the number of slices composing each of the slabs. In this case, the slab including slices of which number is specified is set.

A second aspect of the present invention is concerned with a magnetic resonance imaging system, in which an MR image of an object is obtained by scanning a region of an object previously is located on a positioning image previously acquired from the object. The system, as an interface, comprises a displaying unit, inputting unit, and locating unit. The displaying unit displays the positioning image, and the inputting unit interactively allows two points to be located at desired points on the positioning image. The locating unit locates the region substantially perpendicular to the positioning image on the basis of the located two points. The gist of this configuration is also adapted to a magnetic resonance imaging method as included in the present invention.

Accordingly, it is enough for an operator to place two points at desired locations on a positioning image. This location of the two points will automatically lead to the location of a scanning region, thus shortening a period of time necessary for planning a scan and improving an efficiency of operations for the planning.

For instance, the region is a slab consisting of one or more slices to be scanned for the MR image or a saturation region to be saturated in an MR signal. Preferably, by the inputting unit is configured to repetitively allow each set of the two points to be located at desired points on the positioning image.

A third aspect of the present invention is also directed to an interface function of a magnetic resonance imaging system for obtaining an MR image of an object by scanning a region of the object previously located on a positioning image previously acquired from the object. The system comprises a displaying unit, setting unit, and changing unit. The displaying unit displays a screen including a first window to allow conditions of the region to be given thereto and a second window in which the positioning image is displayed, an icon to which, at least, part of the region parameters being assigned being located in the second window. The setting unit interactively allows the region to be set at a desired position on the positioning image, the region being substantially perpendicular to the positioning image. The changing unit interactively allows the slab to be changed on the basis of the region parameters assigned to the icon. The gist of this configuration is also adapted to a magnetic resonance imaging method as included in the present invention.

Because the icon, to which, at least, part of the region parameters (e.g., slice parameters) are assigned is located together with the positioning image in the same second window, operations needed for specifying various parameters that define the region (e.g., multi-slabs each consisting of one or more slices) become smooth and efficient.

For example, the region is one or more slabs each consisting of one or more slices and the region parameters assigned to the icon includes at least one of the number of slices composing each slab, a thickness of each slice, and a length of each slice. Preferably, the icon is movable in the second window in response to an operator's command.

It is preferred that the changing unit interactively allows each slab to be changed on the basis of the region parameters assigned to the icon. Preferably, the changing unit includes a mouse to be operated and is configured to select one of the region parameters assigned to the icon by clicking the icon with the mouse and to change each slab in one or more of the region parameters by moving in a predetermine direction.

Still preferred is that, by the changing unit, in cases where the selected positioning condition on the icon is the number of slices, the mouse is moved to show movements in an up-and-down direction on the screen. When the selected positioning condition on the icon is the slice length, the mouse is moved to show movements in a lateral direction on the screen. Further, when the selected positioning condition on the icon is the slice thickness, the mouse is moved to show movements in an up-and-down direction on the screen.

It is also preferred that the magnetic resonance imaging system further comprises a switching unit configured to switch over functions of a given button of the mouse responsively to a selection of one of the region parameters on the icon.

BRIEF DESCRIPTION OF THE DRAWINGS

In the accompanying drawings:

FIGS. 4A and 4B illustrate sagittal and coronal images of a lumber vertebra employed by the first embodiment;

FIGS. 5A and 5B explain locating operations performed in the first embodiment;

DETAILED DESCRIPTION OF THE PREFERRED EMBODIMENTS

Referring to the accompanying drawings, preferred embodiments of the present invention will now be described.

First Embodiment

Referring to FIGS. 2 to 8, a first embodiment of the present invention will now be described.

Figure 1:
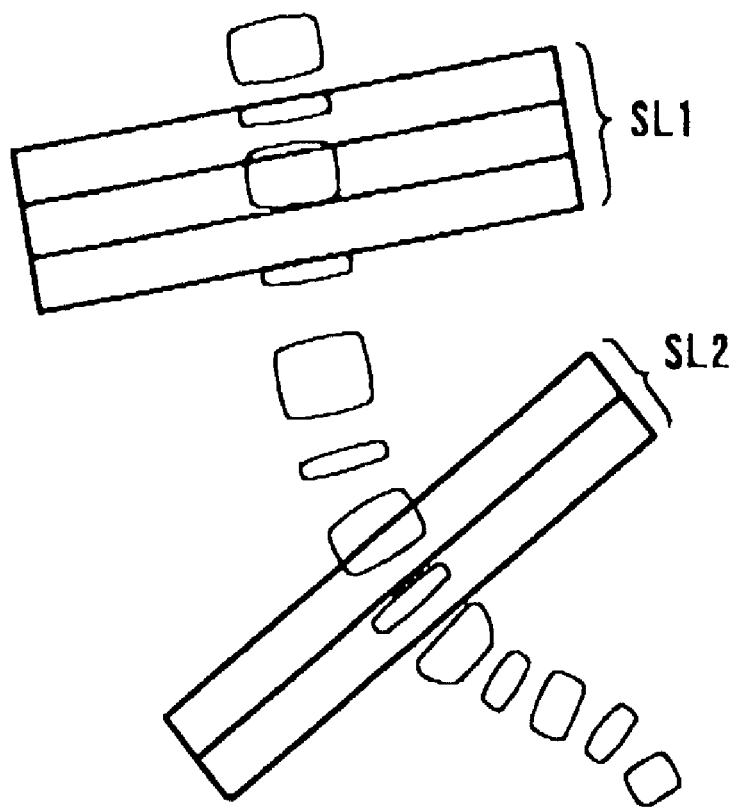
FIG. 1 illustrates a conventional technique of locating slabs.
Figure 2:
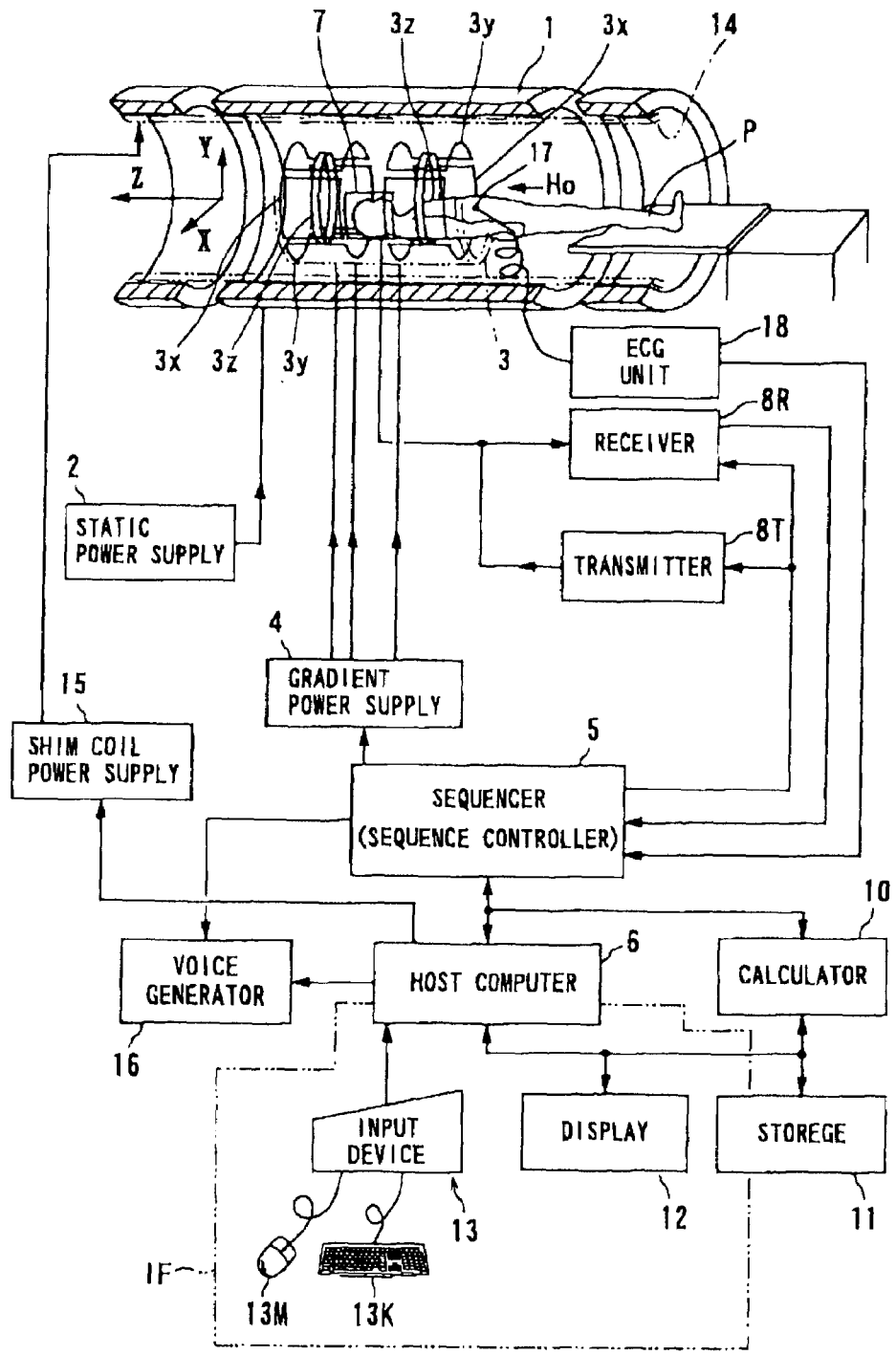
FIG. 2 is the functional block diagram showing an outlined configuration of a magnetic resonance imaging system according to various embodiments of the present invention.

FIG. 2 shows an outlined configuration of a magnetic resonance imaging (MRI) system in accordance with the embodiments of the present invention.

The magnetic resonance imaging system comprises a patient couch on which a patient P as an object to be imaged lies down, static-field generating part for generating a static magnetic field, magnetic-gradient generating part for appending positional information to a static magnetic field, transmitting/receiving part for transmitting and receiving radio-frequency (RF) signals, controlling/calculating part responsible for the control of the whole system and for image reconstruction, electrocardiographing part for acquiring an ECG signal serving as a signal indicative of cardiac phases of the object P, and breath-hold instructing part for instructing the object to perform a temporary breath hold.

The static-field generating part includes a magnet 1 that is of, for example, a superconducting type, and a static power supply 2 for supplying a current to the magnet 1, and generates a static magnetic field Ho in an axial direction (Z-axis direction) within a cylindrical bore (serving as a diagnostic space) into which the object P is inserted for imaging. The magnet 1 includes shim coils 14. A current used to homogenize a static magnetic field is supplied from a shim coil power supply 15 to the shim coils 14 under the control of a host computer to be described later. The couch top of the patient couch on which the object P lies down can be inserted into the bore of the magnet 1 so that the couch top is withdrawn retractably.

The magnetic-gradient generating part includes a gradient coil unit 3 incorporated in the magnet 1. The gradient coil unit 3 has three pairs (kinds) of x-, y-, and z-coils $3x$ to $3z$ used to generate magnetic field gradients that change in strength in the X-axis, Y-axis, and Z-axis directions, that is, the mutually-orthogonal physical-axis directions of the gantry. The magnetic-gradient generating unit further includes a gradient power supply 4 for supplying currents to the x-, y-, and z-coils $3x$ to $3z$. The gradient power supply 4 supplies the x-, y-, and z-coils $3x$ to $3z$ with pulsed currents used to generate magnetic gradients, under the control of a sequencer, which will be described later.

The pulsed currents supplied from the gradient power supply 4 to the x-, y-, and z-coils $3x$ to $3z$ are controlled, whereby magnetic gradients that can be changed in strength in the three physical-axis directions (that is, the X-, Y-, and Z-directions) are mutually synthesized. This synthesis produces a slice magnetic gradient $G_S$ applied in a slice direction, a phase-encode magnetic gradient $G_E$ applied in a phase-encode direction, and a readout (frequency-encode) magnetic gradient $G_R$ applied in a readout direction, so that the gradients $G_S$, $G_E$ and $G_R$ are selectively specified and arbitrarily changed in strength. The slice, phase-encode, and readout directions are logic-axis directions, which are also orthogonal to each other. The magnetic gradients $G_S$, $G_E$ and $G_R$ generated in the logic-axis directions are superposed on the static magnetic field $H_0$.

The transmitting/receiving part includes a radio-frequency (RF) coil 7 located in the vicinity of the object P in the diagnostic space inside the magnet 1, and a transmitter 8T and a receiver 8R both connected to the coil 7. Both of the transmitter 8T and the receiver 8R operate under the control of a sequencer 5 described later. The transmitter 8T supplies the RF coil 7 with an RF current pulse at a Larmor frequency, which will cause a nuclear magnetic resonance (NMR). The receiver 8R receives MR signals (RF signals) via the RF coil 7, and then carries out various kinds of signal processing with the MR signals so that digitized MR data (original data) are produced.

Furthermore, the controlling/calculating part includes a sequencer 5 (also referred to as a sequence controller), host computer 6, calculator 10, storage 11, display 12, input device 13, and voice generator 19.

Of these constituents, the host computer 6 operates on previously memorized software procedures, so that it has the functions of giving the sequencer 5 pulse sequence information, managing the operations of the entire system, and performing an imaging plan, including a positioning plan, according to the present invention.

The sequencer 5, which has a CPU and various memories, is able to store pulse sequence information that has been supplied from the host computer 6. Based on this pulse sequence information, the sequencer 5 controls a series of operations to be performed by the gradient power supply 4, transmitter 8T, and receiver 8R. In parallel with this control, the sequencer 5 temporarily receives digital data produced from MR signals that the receiver 8R has created, and then transfers those data to the calculator 10.

The pulse sequence information includes all information required for operating the gradient power supply 4, transmitter 8T, and receiver 8R according to a desired pulse sequence. The pulse sequence information thus includes the strength, duration, and application timing of pulsed currents that should be applied to the x-, y-, and z-coil $3x$ to $3z$.

As the pulse sequence, a two-dimensional (2D) scan or a three-dimensional (3D) scan can be adopted. Pulse trains can preferably be employed, if they include pulse trains based on an SE (spin echo) technique, an FE (field gradient echo) technique, an FSE (Fast SE) technique, a FASE (Fast Asymmetric SE) technique (also called a "half-Fourier FSE technique"), an EPI (echo planar imaging), and others. The FASE technique is realized based on a combination of the FSE technique and a half-Fourier technique.

The calculator 10 receives digital echo data sent from the receiver 8R via the sequencer 5, and maps those data in a Fourier space (also called a k-space or frequency space) formed by an incorporated memory. The calculator 10 also performs a two-dimensional or a three-dimensional Fourier transform on the mapped data, so that an image in the real space is reconstructed. If necessary, synthesis processing of image data can also be performed by the calculator 10. The calculation of the Fourier transform may be assigned to the host computer 6, not always to the calculator 10.

The storage 11 is able to memorize, in addition to echo data and reconstructed image data, image data that have experienced a wide variety of types of processing. The display 12 is formed to visualize an image. The input device 13 is used to provide the host computer 6 with various types of information including scan conditions, the type of a desired pulse sequence and its parameters, and desired one or more image processing techniques. The input device 13 is provided with a mouse 13M and a keyboard 13K.

The voice generator 19, which composes part of the breath-hold instructing part, is configured to utter, for example, a voice message informing a patient (object) of the start or end of a breath hold in response to a command sent from the host computer 6.

Furthermore, the electrocardiographing part comprises an ECG sensor 17 attached to the patient body to detect an electric ECG signal and an ECG unit 18 that performs various types of processing including the digitization of the detected ECG signal and sends it to both the sequencer 5 and the host computer 6. Both of the host computer 6 and the sequencer 5 use this measured ECG signal as a timing signal during the performance of an imaging scan on the basis of the ECG gating technique.

The entire operation of the above magnetic resonance imaging system will now be described.

In the present embodiment, a lumbar vertebra is assigned to a region to be imaged and subjected to MR imaging, in which imaging slices are set in parallel with desired intervertebral disks present in the lumbar vertebra and images of those slices are obtained. The imaging is carried out based on a multi-slab scan technique. Before this imaging, a scan plan, including a positioning plan for slices to be imaged, is conducted, which will be described below.

Practically, the host computer 6 cooperates with the storage 11, display 12, and input device 13 to conduct the imaging plan in an interactive manner together with an operator. The processing executed by the host computer 6 during the scan plan will be outlined using FIG. 3.

Figure 3:
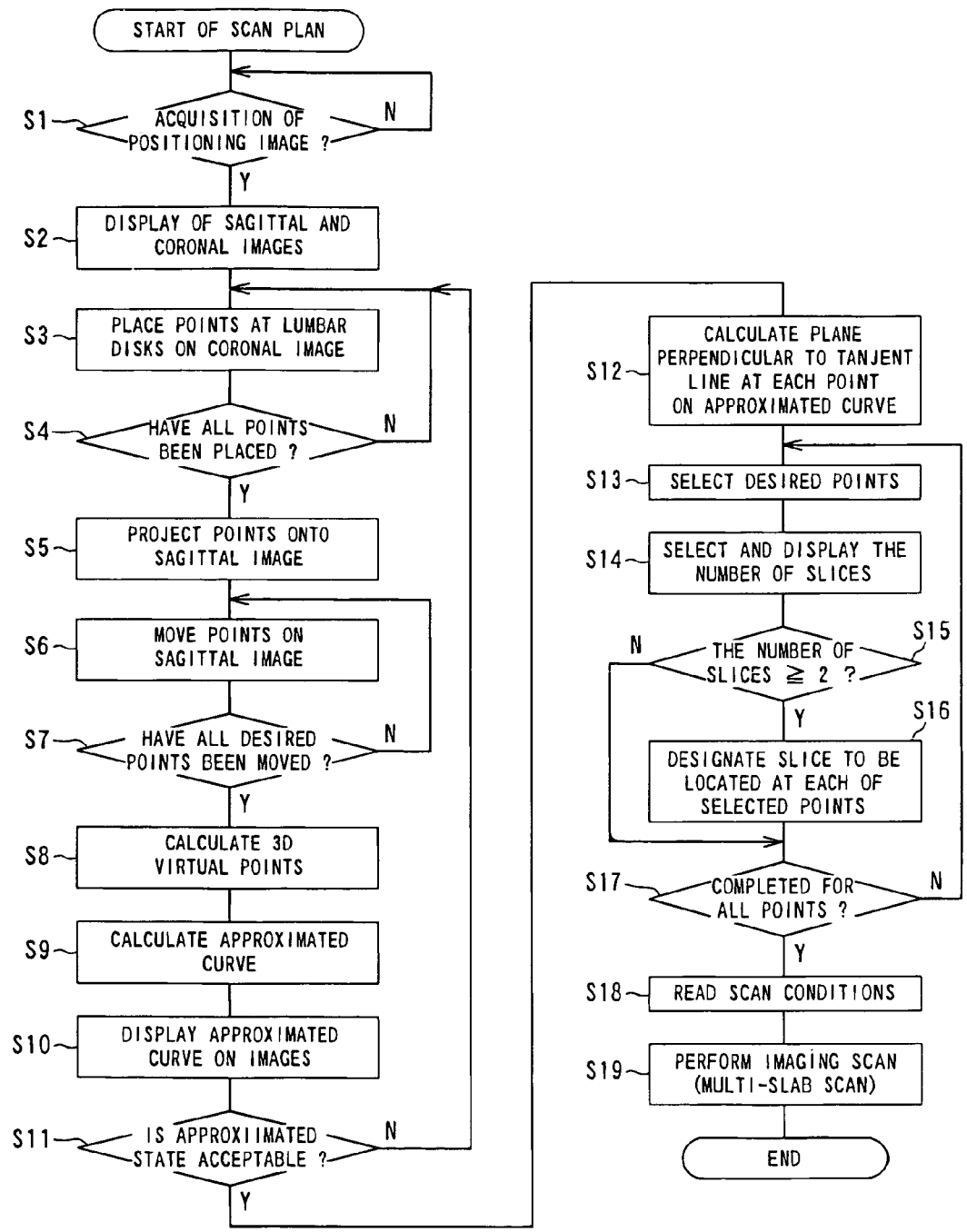
FIG. 3 shows a flowchart for planning a scan, which is carried out by a magnetic resonance imaging system according to a first embodiment of the present invention.

Incidentally, the processing shown in FIG. 3 may be executed by the calculator 10, not always limited to the configuration in which the processing is executed by the host computer 6. Another modified configuration is that the scan plan is executed by a planning apparatus not only placed apart from the magnetic resonance imaging system but also configured into a computer capable of communicating necessary data and information with the magnetic resonance imaging system through the communication network.

Referring to FIG. 3, the processing executed by the host computer 6 will be described. The host computer 6 determines whether or not images for positioning slices to be imaged, or positioning images, should be acquired, while trying to detect a command from an operator, which is issued through the input device 13 (step S1). When the determination shows that the operator desires the positioning images, the host computer 6 instructs the sequencer 5 to scan both a sagittal slice and a coronal slice both including the lumbar vertebra of an object P with the use of a specified pulse sequence (step S2). These scans produce a sagittal image SG and a coronal image CO of the lumbar vertebra, as shown in FIGS. 4A and 4B. Those images are visualized on the same screen of the display 12 in for example a divided form.

There is a modification concerned with the positioning image. The positioning image, which can be adopted in the positioning according to the present invention, is not limited to images of sagittal and coronal slices mutually crossed perpendicularly to each other. Two oblique slices crossed at any angle other than 90 degrees may be used, as long as they contain a target to be imaged, such as the lumbar vertebra.

Then, the intervertebral disks HD of the lumbar vertebra visualized on one of the displayed sagittal and coronal images SG and CO, for example, on the coronal image, are subjected to designation of desired disks. Namely, the host computer 6 responds interactively to commands from the operator to designate plural intervertebral disks HD to which imaging is desired, by individually placing tiny rectangular ROIs (regions of interest) (hereafter, called points PT) on desired disks (steps S3 and S4). Setting the points PT is carried out such that both of the display 12 and the input device 13 are used as a human-side interface to interactively communicate necessary information with the operator via the interface. More practically, the host computer 6 urges the operator to place each point PT on a displayed image on the display 12. Responsively to this, the operator is to operate the input device 13 to designate desired intervertebral disks HD in the vertebral column on the coronal image CO by placing points PT at desired positions.

A modification concerning the above configuration is that, instead of the coronal image, the sagittal image may be adopted to make the operator place points on the sagittal image.

The host computer 6 then calculates so that the positions of all the points PT on the coronal image CO are projected onto and displayed on the sagittal image SG (step S5). Through this projection, the positions of the points PT are projected only in the body-axis direction, so that the projected points PT are initially placed at predetermined positions in the lateral direction on the sagittal image SG.

Then, responsively to instructions from the operator, the host computer 6 operates to adjustably move the position of each points PT from their initial positions in the lateral direction on the sagittal image SG. As a result of it, the position of each point PT can be positioned exactly on each of the desired intervertebral disks HD (steps S6 and S7). On the coronal and sagittal images on the display 12, points PT are displayed in a precise manner to be located on intervertebral disks HD to be imaged, as shown in FIGS. 5A and 5B.

Figure 6:
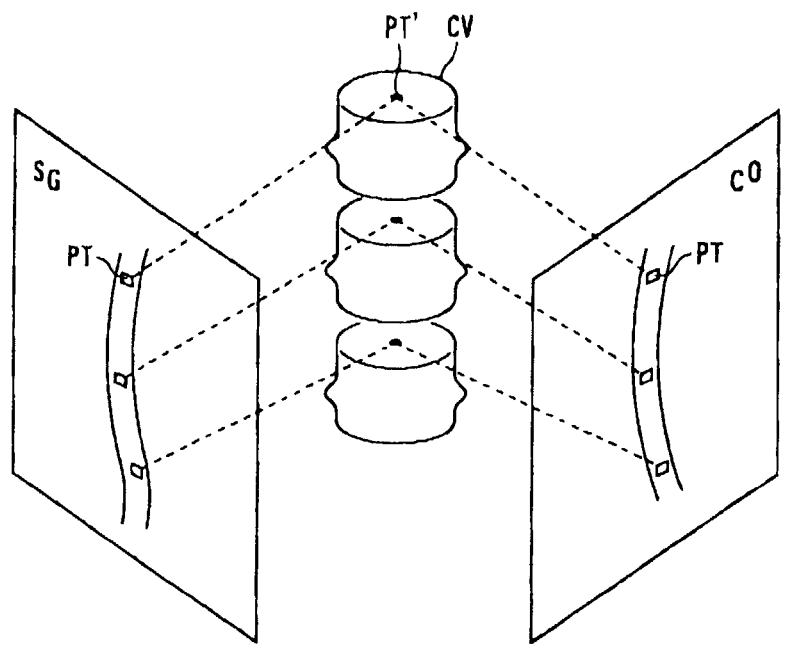
FIG. 6 explains locating operations performed in the first embodiment.

After this setting operation, the host computer 6 calculates each of virtual points PT' uniquely determined three-dimensionally by the points PT on each of the sagittal and coronal images SG and CO, at every pair of points corresponding to each other on both the images (refer to FIG. 6; step S8).

For each of the coronal and sagittal images CO and SG, the host computer 6 further calculates an approximated curve AC made of wire frames that pass through all the virtual points PT' (step S9). These approximated curves AC are obtained by, for example, approximated processing with the use of splines (spline curves) or two-dimensional curve approximation simply passing three points.

Figure 7A:
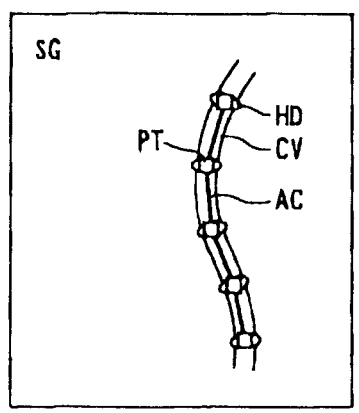
FIGS. 7A and 7B shows approximated curves with wire frames on the sagittal and coronal images, which explains locating operations performed in the first embodiment.
Figure 7B:
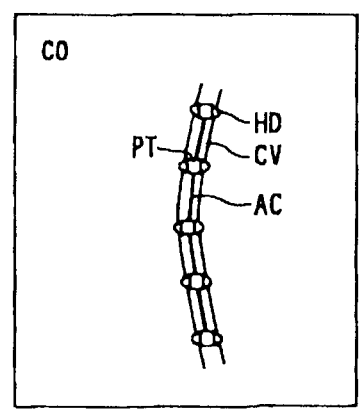

The approximated curves AC calculated based on wire frames are displayed in a superimposed manner on both the sagittal and coronal images SG and CO of the lumbar vertebra, for example, as shown in FIGS. 7A and 7B. In place of this display configuration, the approximated curve may be laid on only either image.

In cases where the operator who observed the displayed approximated curve AC desires that the setting operation should be re-performed, the processing of the host computer 6 will be returned to step S3 (step S11).

At each point PT on the approximated curve AC, the host computer 6 then calculates a plane, or flat surface, perpendicular to a tangent line of the approximated curve AC and memorizes information indicative of the position of the plane (step S12). The thus-calculated plane becomes a slice to be imaged, if a given thickness is given to the perpendicular plane.

The reason why such planes perpendicular to the approximated lines AC based on the wire frames can be used as slices to be imaged is follows. Although vertebral columns, such as a lumber vertebra, are curved three-dimensionally, their curved lines are still continuous. It can therefore be regarded that the directions of the intervertebral disks are also continuously changed. Hence an assumption that each intervertebral disk is perpendicular to the approximated curve AC based on the wire frames is allowed. If complying with this assumption, it is natural to give up calculating the direction of each plane corresponding to each intervertebral disk. Therefore, instead, the wire frames that pass through the intervertebral disks (i.e., approximated curve AC) can be determined, and planes perpendicular to the tangent direction at each point PT can be figured out as being the surfaces representatively depicting intervertebral disks.

As described above, after the perpendicular plane has been determined at every point PT, the host computer 6 operates to interactively control of the number of slices at each point PT (steps S13 to S17). Specifically, in reply to instructions issued from the operator, the host computer 6 selects one of the plural points PT laid on the lumber vertebra (step S13). The host computer 6 then selects a desired number of slices to be scanned at the selected point PT, and displays the contours of one or more slices corresponding to the selected number such that the slices are placed adjacently to and in parallel with the already displayed perpendicular plane (step S14).

To be specific, the number of slices is selected, for example, by selecting a desired number from a pull-down menu displayed on the screen of the display 12. The number of slices, which can be selected by the operator, ranges continuously from one to a plural number (for example, three).

The reason why a plurality of slices can be selected is based on the following clinical two demands. One reason is that comparison between sectional images of a corpus vertebra and an intervertebral disk, which are acquired in the running direction of a vertebral column, is effective for evaluating development of diseases such as herniated disk, so that it is extremely significant to plan scanning of both sections of a corpus vertebrae and an intervertebral disk. The other reason is that there is some need for diagnosing a region of a corpus vertebra CV as well as intervertebral disks.

Figure 8:
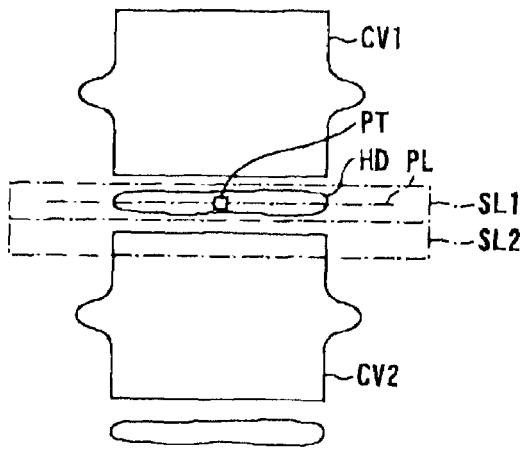
FIG. 8 exemplifies a slab consisting of plural slices, which is located in the first embodiment.

FIG. 8 exemplifies a display state, in which the number of slices that has been selected is two.

Returning to FIG. 3, the host computer 6 determines if or not the number of slices that has been selected is two or more (step S15). If this determination is YES (or, the number of slices is two or more), the host computer 6 selects a slice to be placed at the currently handled point PT (that is, the center of the currently handled intervertebral disk HD) in response to operator's instructions (step S16).

In the example of FIG. 8, according to the forgoing reasons for selection of a plurality of slices, one slice, or the upper slice SL1 in the drawing is selected from the two slices SL1 and SL2, and located at the point PT. In the location of the two slices SL1 and SL2 shown in FIG. 8, the lower slice SL2 is significant for diagnosis of a tomographic image acquired from a one-side position, which is nearer to the intervertebral disk, of the upper corpus vertebra CV2. Like the above example, three slices can be placed. A further modification is that a plurality of slices can be placed with a gap therebetween or gapless.

The foregoing selection of the number of slices and display processing is repeated at each point PT (step S17). Hence, as to each intervertebral disk for which a scan is desired, a desired number of slices, which is selected from a range of given numbers, are located in parallel with each other.

After the location of slices, the host computer 6 operates to receive various other scan conditions required for a multi-slab scan, which are previously set as default values and/or issued responsively to operator's operations (step S18), thus completing the scanning plan.

The host computer 6 then instructs the sequencer 5 to perform the multi-slab scan, thereby providing MR images of the planned slices (step S19).

Accordingly, the magnetic resonance imaging system according to the present invention is able to provide the scan planning function that allows imaging slices to be located at desired positions, such as intervertebral disks, in a more precise and quicker manner, even if a target to be scanned including vertebral columns, such as a lumber vertebra, is curved three-dimensionally.

The scan plan used by the above embodiment requires a plurality of tomographic images (two images in the example of the embodiment), but the use of such images is limited to the designation of intervertebral disks to be targeted. Unlike the foregoing conventional technique that uses a plurality of tomographic images to specify an scan position and a scan angle on each of the images, a time necessary for planning a scan can be shortened greatly. Hence a total imaging time is also shortened down to a practical level in medical care facilities.

Additionally, depending on degrees of medical interest and/or demands for comparison between cross sections of a corpus vertebra and an intervertebral disk, an operator is able to positionally change slices to be scanned at every intervertebral disk. This enables the operator to locate regions to be scanned, more steadily. Further, re-scanning can be almost avoided, thus improving a patient throughput and alleviating operational work imposed on operators.

The present invention is not limited to the configurations described above, and there are various modifications that can still be applied to the present invention. For example, a first modification relates to placing points at intervertebral disks In the foregoing embodiment, points placed on one image (e.g., coronal image CO) are projected onto the other image (e.g., sagittal image SG) in the body-axis direction. Alternatively, an operator is able to place points at desired positions on both the images in an interactive way through the processing shown in steps S3 and S4 of FIG. 3. Moreover, in cases where a desired intervertebral disk to be observed exists at only one place, it is also preferred that points are automatically located, in addition to the intervertebral disk itself, on the upper and lower sides thereof in a direction orthogonal with the longitudinal direction of the disk. That is, the total of three slices are automatically placed over the intervertebral disk desired, thus simplifying the operations necessary for scan planning.

Second Embodiment

Referring to FIGS. 9 to 20, a second embodiment of the present invention will now be described.

A magnetic resonance imaging system employed in the second embodiment has the same configuration as that of the first embodiment (refer to FIG. 2), but has a different interface for planning a scan. The interface is functionally configured by the host computer 6, storage 11, display 12, and input device 13 (refer to a reference IF in FIG. 2).

Figure 9:
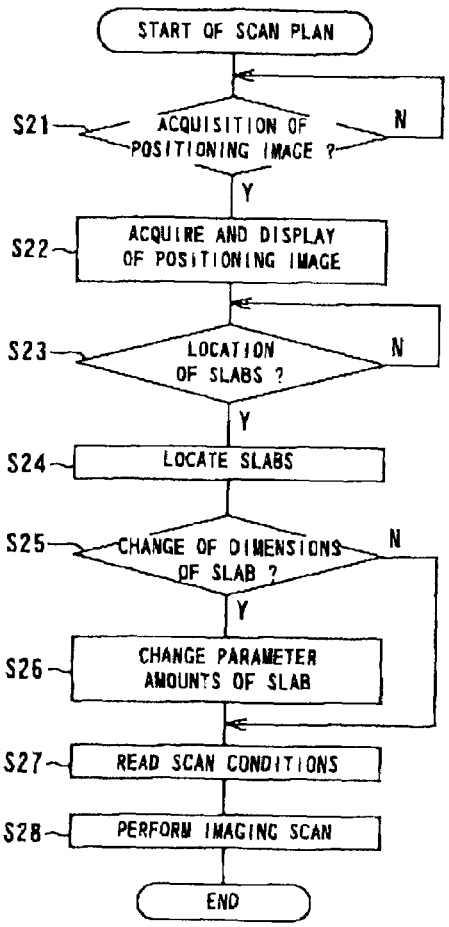
FIG. 9 is a flowchart outlining for planning a scan, which is carried out by a magnetic resonance imaging system according to a second embodiment of the present invention.

A flowchart shown in FIG. 9 outlines the processing of a scan plan interactively carried out between the interface and an operator. This processing includes processes for acquisition and display of a positioning image (steps S21 and S22), processes for locating one or more slabs each consisting of one or more slices (steps S23 and S24), processes for changing dimensions of the slices that have been designated once (steps S25 and S26), and processes for performing an imaging scan (steps S27 and S28). These processes will be explained in detail by turns.

(A: Scanning Positioning Image)

Figure 10:
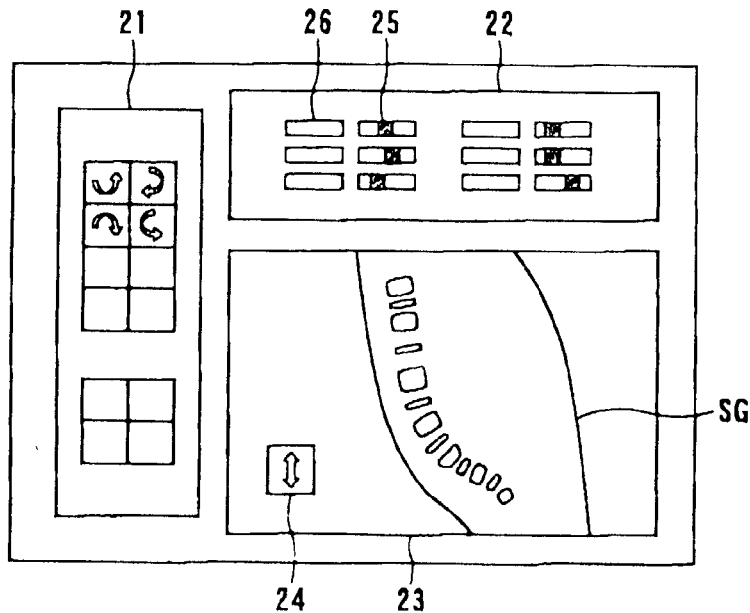
FIG. 10 pictorially shows the screen of a display in the second embodiment.

In response to an operator's start command issued through the input device 13, the host computer 6 operates to cause the sequencer 5 to perform a predetermined pulse sequence for a preparatory scan (step S21 in FIG. 9). The performance of the pulse sequence produces MR signals acquired by scanning a sagittal section along a region of a vertebral column of an object P. Thus, from the acquired MR signals, the calculator 10 reconstructs a sagittal image. The data of the sagittal image is then memorized by the storage 11, while the sagittal image is displayed on the display 12 as a positioning image, as shown in FIG. 10 (step S22 in FIG. 9). Using this positioning image, one or more slices crossing the positioning image (i.e., sagittal image SG) are designated as slices to be scanned by the imaging scan and their slices are changed in position or angle, if necessary.

After the scanning, a screen shown in FIG. 10 is provided on the display 12. The screen includes windows 21 to 23. In a lower right area of the screen, there is provided the display window 23 in which the sagittal image SG serving as the positioning image is present. In a central area of the sagittal image SG, the vertebral column of the object P is depicted. On the sagittal image SG, an icon 24 for setting/changing slice parameters is laid, which will be later described.

In the upper right area of the screen, the window 22 is present, in which various kinds of sub-windows for specifying slice parameters (the number of slices, slice thickness, slice length and others) are placed.

In the left area of the screen, the window 21 is present, in which displayed are sub-windows to be clicked to move (rotate, enlarge, contract, or the like) the image SG displayed in the window 23 and/or buttons to be clicked to switch over setting modes.

(B: Locating Slices)

Locating slices (steps S23 and S24 in FIG. 9) follows the acquisition and display of the sagittal image. This location is realized in an interactive manner between the interface and an operator. During the location of slices and later-described changes (or adjustments) of dimensions of the slices in their positions and angles, the patient P is kept being laid on the patient couch, with no gradient and RF pulse applied.

Figure 11:
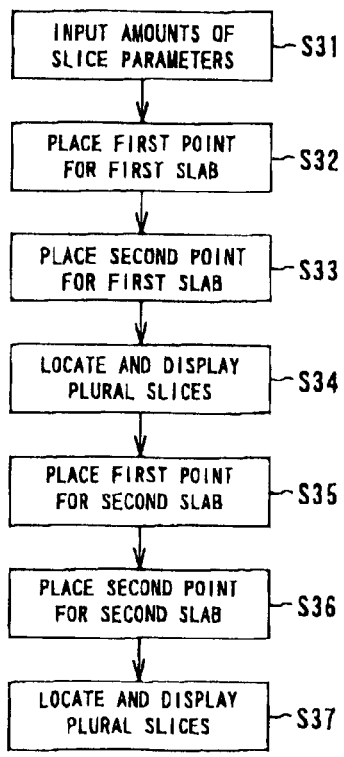
FIG. 11 outlines a flowchart for locating multi-slabs on a positioning image.

Practically, a plurality of slices that compose one or more slabs, which are subjected to the imaging scan carried out after the scan plan, are located based on the procedures shown in FIG. 11, which are executed by the host computer 6.

The sagittal image SG that has already been described is used for this location of slices. First, at step S31, an operator inputs, to the interface, amounts of desired slice parameters that include a slice thickness, slice length, the number of slices, and others applied to the imaging scan carried out later. Practically, the operator uses the keyboard 13K to input numerical values into given frames 26 placed in the window shown by the window 22 or uses the mouse 13M to move bars 25 to desired scales in the window.

Figure 12A:
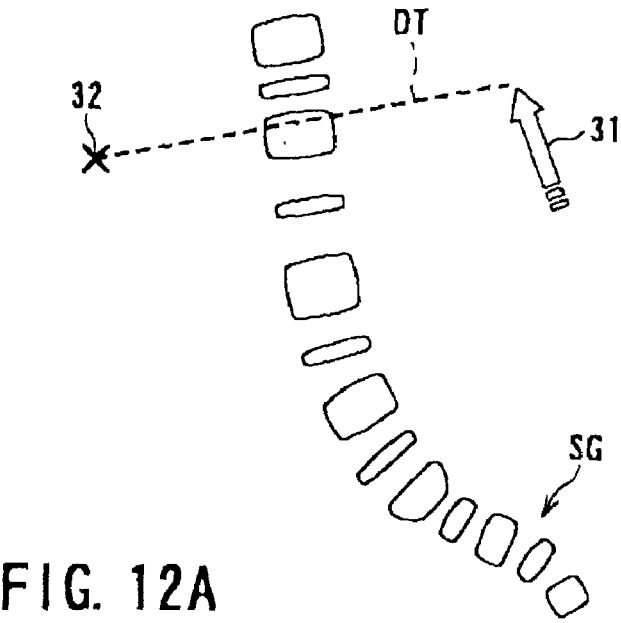
FIGS. 12A and 12B show procedures for locating slabs by inputting each pair of two points.

Then, in response to an operator's command, the host computer 6 operates to place a first point for a first slab on the sagittal image SG (step S32). Specifically, the operator uses the mouse 13M on the input device 13 clicks a point 32, or the first point, on the sagittal image SG, as shown in FIG. 12A.

On specifying the point 32, the host computer 6 works so as to automatically represent both of a dotted line DT and a cursor (i.e., pointer) 31 along an initial direction and at an initial position on the sagittal image SG. The cursor 31, which is movable by the mouse 13M, connects the point 32 and the tip of the cursor 31.

Then, the tip of the cursor 31 is moved to a desired position, the operator operates the mouse 13M to click at the desired position, or a second point for the first slab, on the sagittal image SG (step S33). In replay to the operator's click, the host computer 6 will automatically locate and display a plurality of slices 34 between both the points 32 and 33, as illustrated in FIG. 12B (step S34).

To be specific, using, as a center line CT, a straight line mutually connecting both the points 32 and 33, a slice region that consists of plural slices 34 according to the preset slice parameters (including the number of slices, slice thickness, and slice length) is placed symmetrically to the center line. In this location, in a direction along the center line CT, the center of the slicing region (plural slices 34) is placed at the center of center line CT. As a result, a first slab 34S composed of plural slices 34 is designated at a desired area on the sagittal image SG. Each slice is set to the same thickness and length.

Incidentally, in the above procedure, each set of two points 32 and 33 may be placed at any points on the sagittal image SG. Particularly, one advantageous way is to locate the two points 32 and 33 at both ends of desired intervertebral disks, as shown in FIG. 12B. This way is relatively helpful for making slices, or slab, locate as parallel with each disk as possible.

Figure 12B:
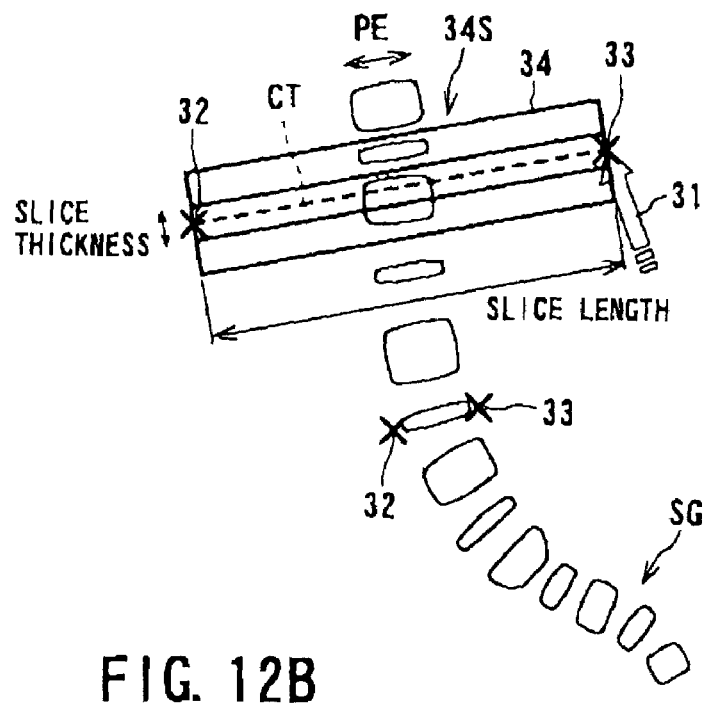

In addition, it is also preferable that the length direction of slices to be displayed on the sagittal image SG is assigned to a phase encoding direction PE in performing an imaging scan for acquiring echoes for MR images, as shown in FIG. 12B. Setting the phase encoding direction like this is effective for reducing an aliasing noise on MR images.

Figure 13A:
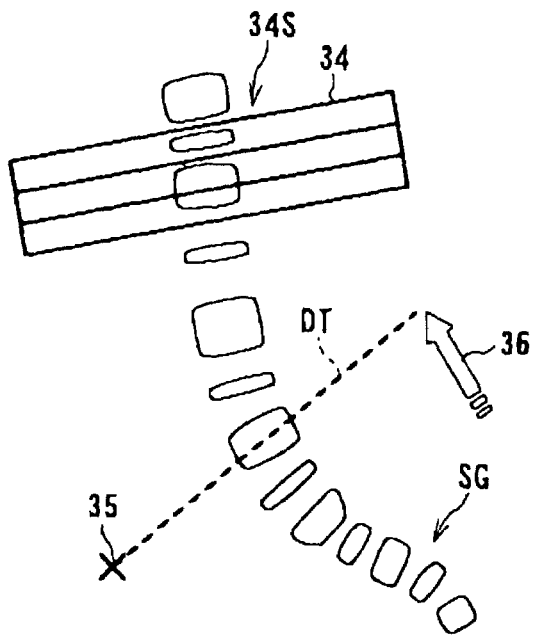
FIGS. 13A and 13B show procedures for locating slabs by inputting each pair of two points.
Figure 13B:
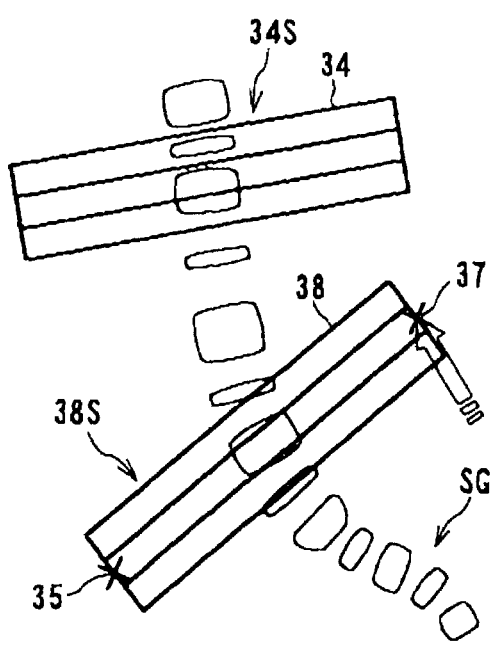

Like the foregoing procedures in steps S32 to S34, a first point 35 for a second slab is placed (step S35), as illustrated in FIG. 13A, in which a cursor 36 connected with the first point 35 through a dotted line DT. Then, as shown in FIG. 13B, a second point 37 for the second slab is placed by the operator in the same manner as the above (step S36). In replay to this operation, the host computer 6 will automatically locate and display a plurality of slices 38 between both the points 35 and 37, as illustrated in FIG. 13B (step S37). As a result, a second slab 38S composed of plural slices 38 is designated at another desired area on the sagittal image SG.

The information indicative of positions and angles of the plural slabs thus placed is stored in the storage 11.

According to the present embodiment, both of the first and second slabs 34S and 38S can be located using one set of slice parameters in common. Furthermore, in the present embodiment, the four points 32, 33, 35, and 37, which are needed for locating the two slabs 34S and 38S can be placed in sequence on the sagittal image, or the positioning image.

(C: Changing Dimensions of Slices)

Figure 14:
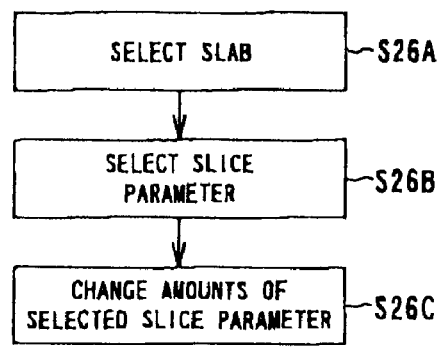
FIG. 14 outlines procedures for changing (adjusting) amounts of slice parameters of located slabs.

After locating the slices that make up of plural slabs, the host computer 6 proceeds to step S25 to determine whether or not it is required to change the conditions of slices in an interactive manner with the operator. If the determination of YES (that is, it is required to change amounts of the slice parameters entirely or partly), the processing is moved to step S26, the detailed procedures of which are shown in FIG. 14. Images presented in the display window 23 in reply to the procedures are exemplified in FIGS. 15, 16, and 18–20.

In the following, of the conditions of slices, the number of slices is chosen as a slice parameter to be changed, and changing "the number of slices" after it was once set will be exemplified in detail.

Figure 15:
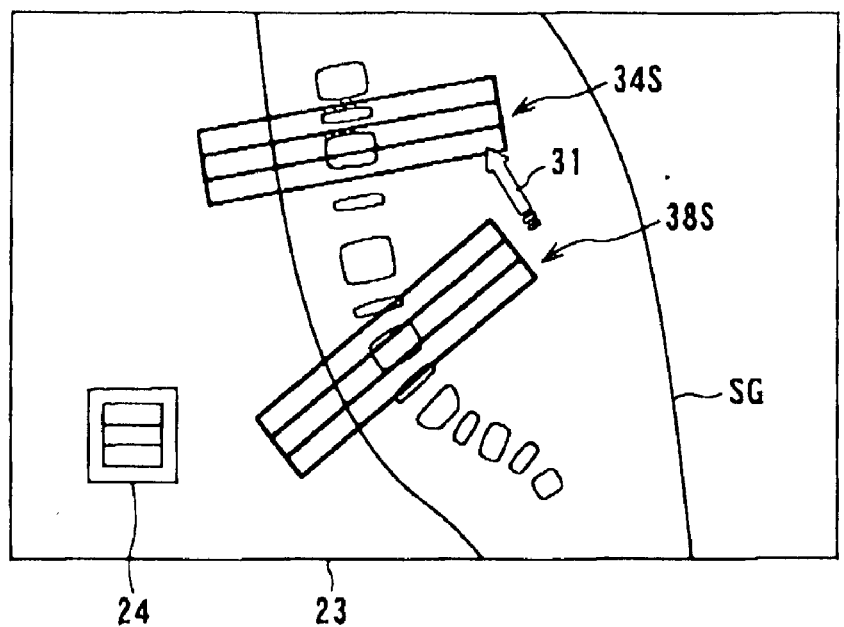
FIG. 15 shows procedures for adjusting slabs with use of an icon displayed on the positioning image.

First, at step S26A of FIG. 14, the host computer 6 operates to select a slab to be changed in the number of slices in an interactive manner with the operator. In detail, as shown in FIG. 15, the mouse 13M is used to move the cursor 31 to a change-desired slab, and is clicked, thus the slab being selected.

Figure 16:
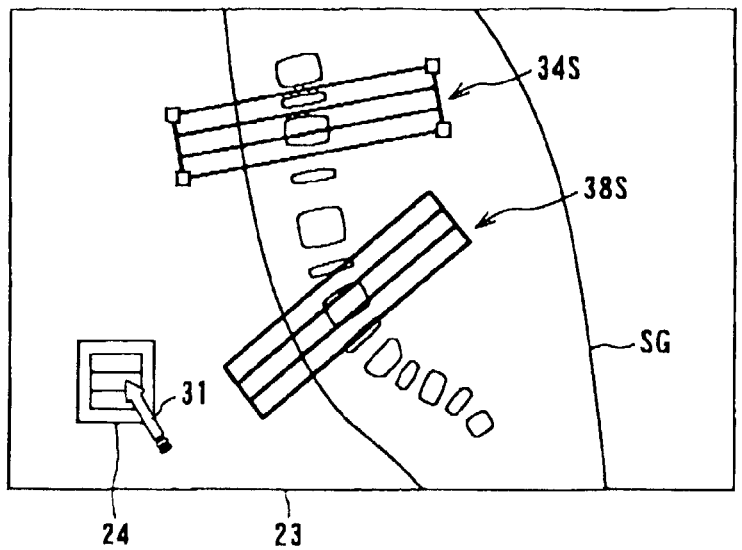
FIG. 16 shows procedures for adjusting slabs with use of an icon displayed on the positioning image.

Then at step S26B, the host computer 6 selects a slice parameter using instructions from the operator. This selection is to decide which one of the plural slice parameters (i.e., slice thickness, slice length, the number of slices, and others) should be subjected to changes in amounts. As a practical way, as shown in FIG. 16, the host computer 6 moves the cursor 31 to the icon 24 for setting conditions, before accepting several times of clicks of a right button R of the mouse 13M (i.e., right clicks; refer to FIG. 17). Responsively to those clicks, the icon 24 is able to change its functions 241 to 244 with the help of the host computer 6 in a circulatory order illustrated in FIG. 17.

One function 241 is used for changing the thickness of a slice, another function 242 is used for changing the length of a slice, and another function 243 is used for simultaneously changing both of the thickness and length of a slice. The remaining function 244 is directed to changing the number of slices.

The host computer 6 receives a signal indicative of which function to use from the icon 24 and the mouse 13M. Depending on a function that has been chosen, the host computer 6 will switch over left-button (L) functions of the mouse 13M. Changing amounts (value, distance, and others) of a designated slice parameter (in the present embodiment, the number of slices, a slice length, or a slice thickness) is assigned to the left button L. Hence, the host computer 6 serves as a switching unit for switching over the functions of the left button L of the mouse 13M.

When changing values of the number of slices is desired, the function 244 of the icon 24 is used. Hence, the operator repeats click operations until the function 244 appears on the icon 24.

Then, at step S26C, the host computer 6 operates to accept and set a corrected-amount slice parameter interactively with the operator on a screen shown in FIG. 9. This operation is carried out such that the operator moves the mouse 13M upward and downward with a left click of the mouse 13M kept. Specifically, with the cursor 31 on the icon 24, the mouse 13M undergoes its left click, thereby the cursor 31 being fixed thereat. With the cursor 31 fixed on the icon 24, the operator moves the mouse 13M upward and downward.

In response to upward and downward movements of the mouse 13M, the host computer 6 operates to change the number of slices displayed on the window 23. In the present embodiment, if the mouse 13M is moved upward, the host computer 6 increases the number of displayed slices in compliance with its moved amount.

Figure 18:
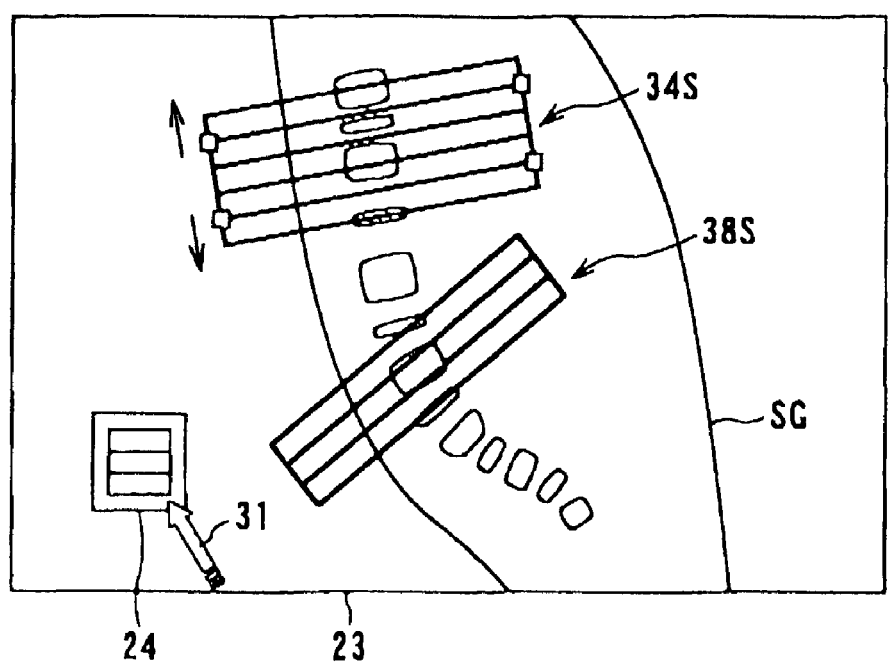
FIG. 18 shows procedures for adjusting slabs with use of an icon displayed on the positioning image.

FIG. 18 shows an example, in which the mouse 13M has been moved upward to increase the number of slices up to five from three slices shown in FIG. 16.

By contrast, when the mouse 13M is moved downward, the host computer 6 detects a downward movement of the mouse 13M and decreases the number of displayed slices in compliance with its moved amount.

In this increasing and decreasing case, as typically shown in FIG. 18, both of a slice thickness and a slice length that have been attained before the changes are still maintained even after the changes. The slices that are increased or decreased are always added to the original slices so as to maintain an entirely symmetric slab form to the centerline thereof. That is, when increasing slices, slices are symmetrically added to both sides of the original ones, one by one, two by two, three by three, or others. In contrast, when decreasing slices, slices are symmetrically reduced from both sides of the original ones, one by one, two by two, or others. During the above operations, the icon 24 is kept at the same place on the window 23.

Figure 19:
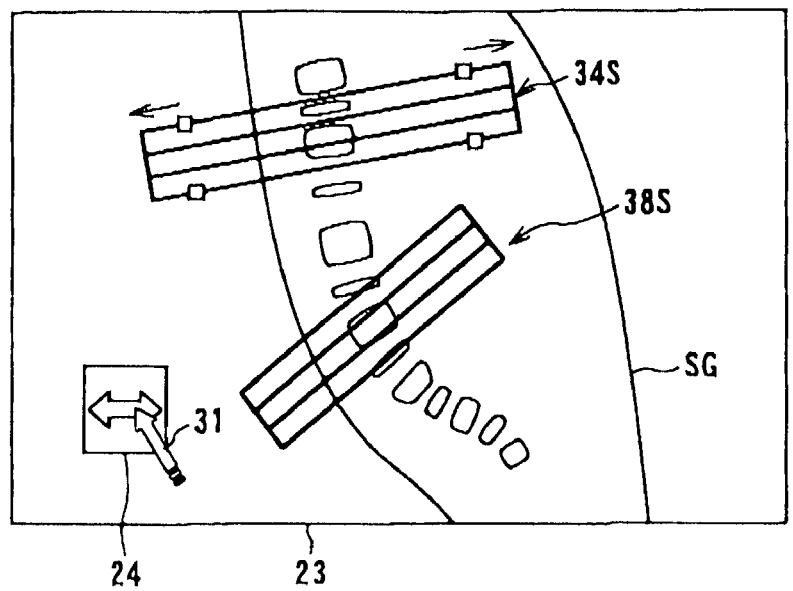
FIG. 19 shows procedures for adjusting slabs with use of an icon displayed on the positioning image.
Figure 20:
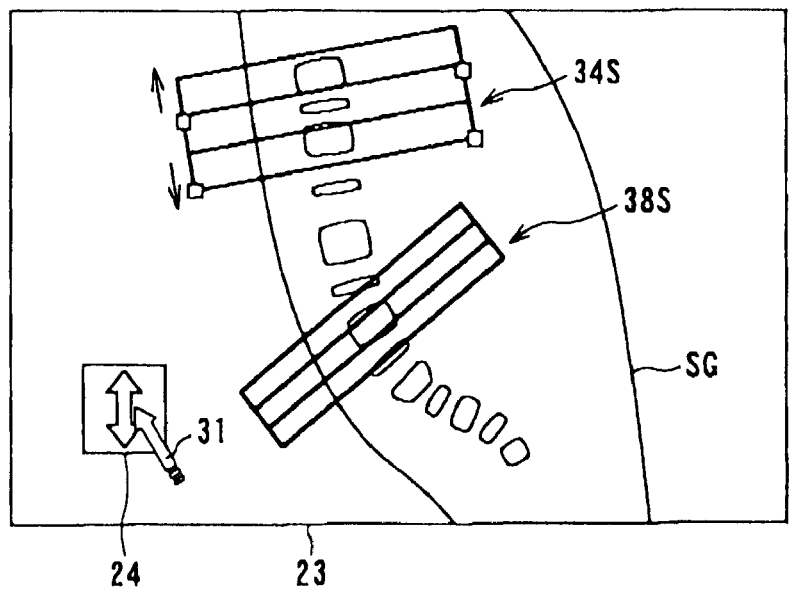
FIG. 20 shows procedures for adjusting slabs with use of an icon displayed on the positioning image.

In the present embodiment, slice parameters to be changed in amounts is not limited to the number of slices, but can be performed with changing a slice length and a slice thickness. FIG. 19 illustrates changes of slice lengths, while FIG. 20 illustrates changes of slice thicknesses.

Changing slice lengths can be done after the selection of the function 242 at the icon 24 on the window 23 (refer to FIG. 19). An operator operates the mouse 13M to move the cursor 31 on the icon 24, and clicks the left button of the mouse 13M, during a period of the left click operation the mouse 13M is moved right and left. In response to such a rightward or leftward movement of the mouse 13M, the host computer 6 changes the lengths of the slices belonging to a desired slab, as illustrated by arrows in FIG. 19.

In the present embodiment, a rightward movement of the mouse 13M causes the lengths of the slices to be lengthened, whilst a leftward movement of the mouse 13M causes the lengths thereof to be shortened. Lengthened or shortened amounts depend on moved distances of the mouse 13M. Changing slice lengths are reflected at a time into all the slices of a selected slab.

Figure 17:
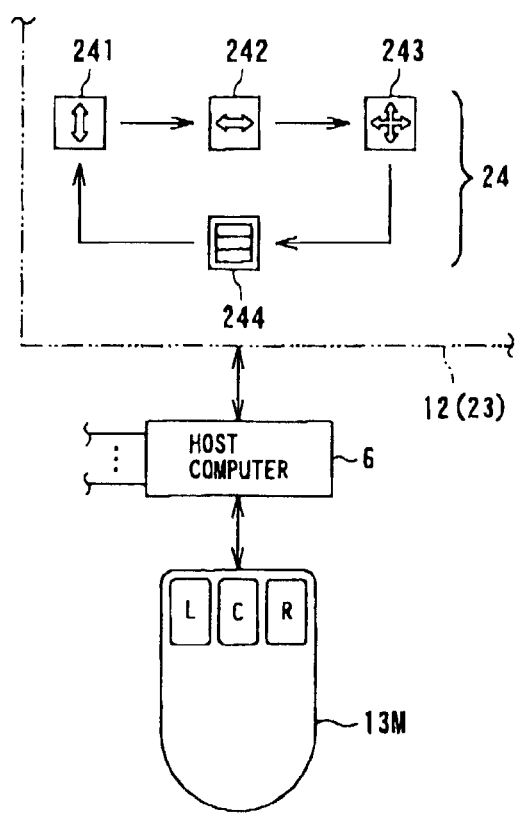
FIG. 17 explains a circulation of functions assigned to a certain button of the mouse.

Like the above, changing slice thicknesses can be done after the selection of the function 241 at the icon 24 on the window 23 (refer to FIG. 17). In the same procedures as those in changing slice lengths, moving the mouse 13M in the right and left directions makes it possible that slice thicknesses of all the slices included in the same desired slab are changed, as pictorially shown in FIG. 20. Changing slice thicknesses can be performed dependently of changing the number of slices.

As described above, the icon 24 that has been displayed on the positioning image, such as a sagittal image, is used by an operator to change desired one or more slice parameters (conditions).

Incidentally, the above icon 24 is not always used for only changing amounts of slice parameters, but can be used to initially set amounts of slice parameters before the display of slabs on the display. Further, instead of using the icon 24, the window 22 can be used as well to change amounts of slice parameters. The position of the icon 24 can be moved to any position on the sagittal image through drag-and-drop operations while a predetermined button on the keyboard 13K etc. is pushed.

(D: Imaging Scan)

After completion of setting the slice parameters, the host computer 6 responds to an operator's command to start an imaging scan, thus instructing the sequencer 5 to perform a predetermined pulse sequence for the imaging scan. The sequencer 5 performs the pulse sequence, in which the strengths and timings of both of RF pulses and gradient pulses are controlled to scan the slices of the slabs located based on the above procedures B and C.

Images of the slices obtained by the imaging scan can selectively be displayed in the window 23 of the screen of the display 12 in response to an operator's command. Doctors use the images to diagnose diseases such as herniated disk.

As configured and operated above, the interface according to the present second embodiment provides various advantages.

First of all, only placing two points on the positioning image will automatically lead to setting a slab. And continuously placing another set of two points on the positioning image will automatically lead to setting another slab. It is therefore possible to continuously locate slabs, thus improving efficiency in locating slabs, compared to the conventional, thus contributing a whole imaging time of an object.

Second, the icon 24 as well as the window 23 for setting and changing amounts of slice parameters can be used, so that an operator is able to smoothly (i.e., quickly and precisely) determine amounts of slice parameters. Particularly, in cases where frequently used slice parameters are used, using the icon 24 is very effective, because it is enough for the operator only to use the same mouse 13M, not required to move the operator's hand between the mouse 13M and the keyboard 13K. Thus, burdensome operations of touching both the mouse 13M and the keyboard 13K, like the conventional, are avoided.

Third, the icon 24 is displayable on a positioning image. Hence, it is enough that an operator watches only the same window 23, thereby providing a smooth operation for setting slice parameters. Unlike the conventional, it is not necessary to move a cursor between, if explained in FIG. 10, the positioning image SG (window 23) and the condition-setting window 22.

Fourth, the single 24 allows both the number of slices and slice thicknesses to be changed with the mouse 13M alone, thus being simplified in operations and being highly convenient. In the conventional, to change the number of slices and slice thicknesses on a sagittal image involves the same movement directions on the screen (refer to FIGS. 18 and 20), so that the operations were complicated and burdensome.

Fifth, setting and changing amounts of slice parameters using the icon can be done slab by slab, being speedy in positioning slices and highly convenient.

Sixth, the icon 24 is highly functional, because the icon makes it possible to selectively display one from a plurality of slice parameters and determine the amount of the selected slice parameter. In other words, compared to a situation where an icon is displayed correspondingly to a slice parameter in a one-by-one correspondence (for example, an icon dedicated to setting only slice thicknesses and another icon dedicated for setting the number of slices), the icon 24 according to the present embodiment has multiple functions. By way of example, as described before, a plurality of slice parameters, such as slice thicknesses, slice lengths, and the number of slices, can be set and changed with the use of the one icon 24.

The multi-functional icon promotes more effective use of the limited-size screen on the display. Further, the icon 24 itself is movable to any position on the positioning image, thereby providing an easy-to-observe target image (such as an image of the lumber vertebra) without being hidden by the icon.

According to the present embodiment, there are still various kinds of modifications.

A first modification is the configuration in which the icon 24 can be placed outside the display window 23, not limited to the inside thereof in which the positioning image SG is present.

A second modification concerns the parameters of each slice which are adjustable. In the second embodiment, the icon 24 has been configured to set amounts of both its slice thickness and length. In addition to those two parameters, the remaining dimension, or the length along the depth direction in the figures, may be added so that it can be adjustable in the foregoing changing process.

More significantly, the interface function according to the second embodiment can be reduced into practice with the use of a conventional technique for changing slices, without using the foregoing changing process described by the second embodiment.

Further, part of the interface function according to the second embodiment can be practiced in a combined manner with the locating technique described by the first embodiment. Precisely, a plurality of slabs each consisting of one or more slices are three-dimensionally located based on the locating technique described by the first embodiment, and then the slabs are adjusted in slice sizes and the number of slices based on the changing slice technique (C) described by the second embodiment.

Third Embodiment

Figure 21:
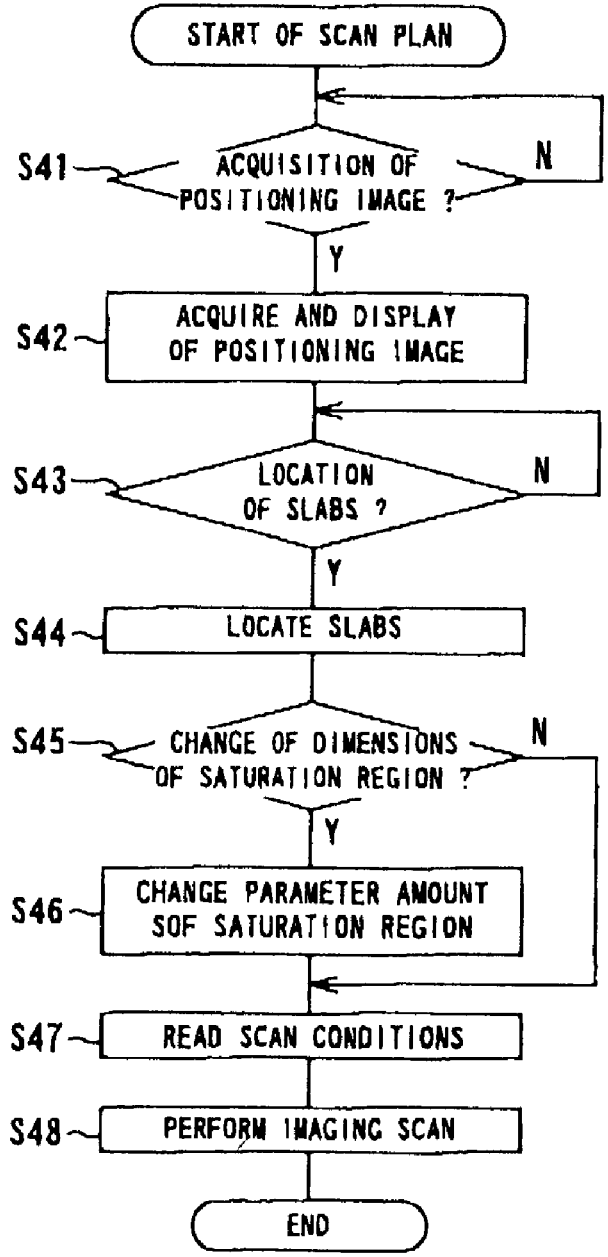
FIG. 21 is a flowchart outlining for planning a scan, which is carried out by a magnetic resonance imaging system according to a third embodiment of the present invention.
Figure 22:
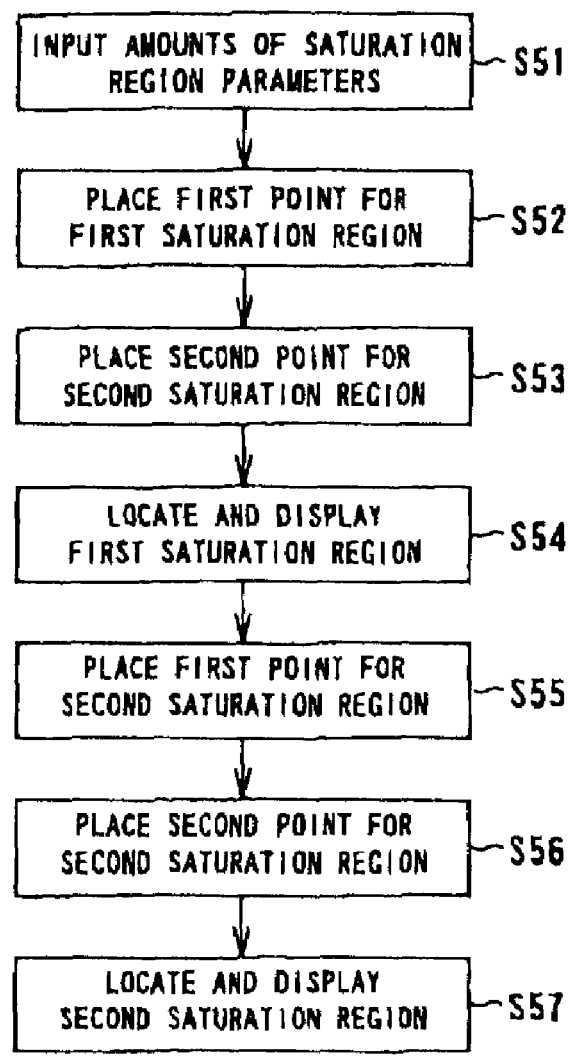
FIG. 22 outlines a flowchart for locating saturation regions on a positioning image.

Referring to FIGS. 21 to 23, a third embodiment of the present invention will now be described.

A magnetic resonance imaging system employed by the third embodiment has the same configuration as that of the first embodiment (refer to FIG. 2), but has a different interface for planning a scan. That is, the interface is modified from the second embodiment in that one or more saturation regions are located together with slices (composing slabs). The interface is functionally configured by the host computer 6, storage 11, display 12, and input device 13.

A flowchart shown in FIG. 21 outlines the processing of a scan plan interactively carried out between the interface and an operator. This processing includes processes for acquisition and display of a positioning image (steps S41 and S42), processes for locating one or more slabs each consisting of one or more slices (steps S43 and S44), processes for locating one or more saturation regions (steps S45 and 46), and processes for performing an imaging scan (steps S47 and S48).

The processes for acquisition and display of a positioning image (steps S41 and S42) are carried out in the similar way to those in the first embodiment. Accordingly, the display 12 provides the display of a planning image, which is similar to that in the second embodiment (refer to FIG. 10), but different from that in that there is no icon 24 that has shown in FIG. 10.

The processes for locating one or more slabs (steps S43 and S44) are then carried out in the same way as that in the second embodiment.

The processes for locating one or more saturation regions (steps S45 and 46) are then carried out as follows. This locating processing can be done after the location of slabs, as in this embodiment, or before the location of slabs. If there is no necessity of using saturation regions, the present locating processes can be omitted from the interface function. Still, by way of example, pressing a preset button in the region 21 shown in FIG. 10 makes it possible to change, at any time, the mode for locating slices to another mode for locating saturation regions.

Practically, the host computer 6 executes the location of saturation regions in an interactive way with an operator according to the processing shown in FIG. 22.

The sagittal image (positioning image) SG of a lumbar vertebra is still present in the display window 23, as it is after having been subjected to the location of slabs. This sagittal image SG is continuously used for locating saturation regions.

With the sagittal image SG displayed, saturation conditions are given by an operator as practical values or amounts (step S51). The saturation conditions include a desired width of a saturation region.

Figure 23A:
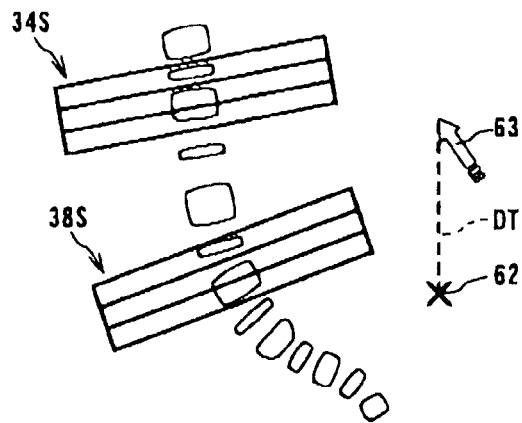
FIGS. 23A to 23C show procedures for locating saturation regions by inputting each pair of two points on a positioning image.

In response to an operator's command, the host computer 6 places a first point 62 for a first saturation region at a desired position on the sagittal image SG, as shown in FIG. 23A (step S52), like the location of the first slab described in the second embodiment.

Figure 23B:
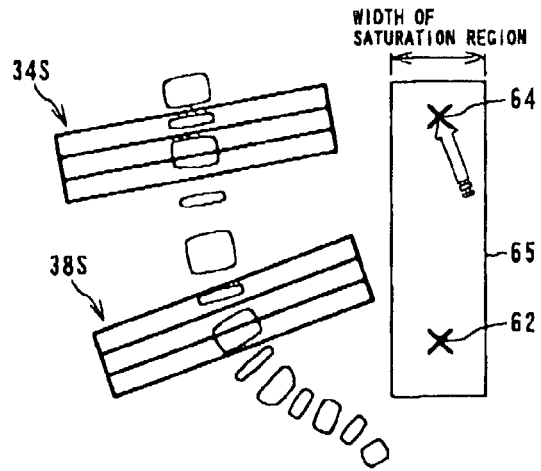

Responsively to another operator's command, the host computer 6 operates to place a second point 64 for the first saturation region at another desired position (step S53; refer to FIG. 23B). For placing the second point 64, an automatically visualized pointer 63 and a dotted line DT connecting the tip of the pointer 63 to the first point 62 is helpful (refer to FIG. 23A).

After placing both the points 62 and 64, the host computer 6 places on the sagittal image SG a first saturation region 65 having a predetermined width according to the given saturation condition (step S54). In detail, the saturation region 65 is formed into a rectangular shape symmetry to a centerline connecting both the points 62 and 64.

Figure 23C:
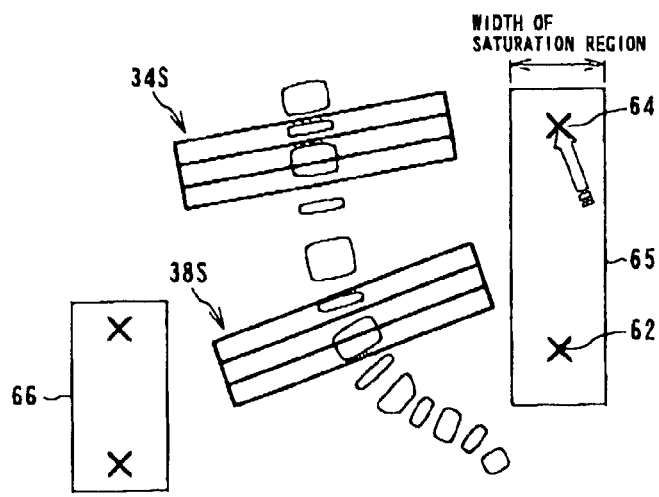

In the same way as the above, a second saturation region 66 is located by specifying another set of two points through the processes at steps S55 to S57 (refer to FIG. 23C).

When the above preparation is completed, an imaging scan using a desired pulse sequence is carried out to produce MR images at the designated slices. During the scanning, the designated one or more saturation regions undergo previous application of RF saturation pulses. Hence magnetic spins that are present in the saturation regions are previously flopped, reducing MR signals to be acquired by the imaging scan.

According to the third embodiment, only placing two points on the positioning image will automatically lead to setting a saturation region. And continuously placing another set of two points on the positioning image will automatically lead to setting another saturation region. It is therefore possible to continuously locate saturation regions, thus improving efficiency in locating saturation regions, compared to the conventional, thus contributing a whole imaging time of an object.

By the way, part of the interface functions according to the third embodiment can be practiced in a combined manner with the locating technique described by the first embodiment. Precisely, a plurality of slabs each consisting of one or more slices are three-dimensionally located based on the locating technique described by the first embodiment, and then one or more saturation regions are located based on the locating technique described by the third embodiment.

Although the embodiments described above contain many specificities, these should not be construed as limiting the scope of the present invention but as mealy providing illustrations of some of the presently preferred embodiments of the present invention. The person skilled In the art can alter or modify the present invention into a variety of different modes without departing from the scope of the appended claims and their equivalents.

For example, the present embodiment has been described about the magnetic resonance imaging system having the cylindrical-bore gantry, but any type of system can be adopted in the present invention, not limited to the shape of the gantry and the applied direction of a static magnetic field. Such an example can be shown as a magnetic resonance imaging system with an open type of gantry.

What is claimed is:

1. A magnetic resonance imaging system in which an object to be imaged is subjected to scanning to obtain an MR image, the scanning being applied to a region of the object, a sub-region to be imaged being previously located on a positioning image of the object, the system comprising:
   a displaying unit configured to display the positioning image;
   a locating unit configured to repetitively allow an operator to locate two points at desired points on the positioning image; and
   a setting unit configured to set a further sub-region substantially perpendicular to the positioning image on the basis of the located two points, the further sub-region thus located being set by the setting unit being a saturation sub-region to be saturated with an MR signal before scanning the region for the MR image of the sub-region to be imaged.

2. The magnetic resonance imaging system of claim 1, wherein the sub-region to be imaged is also set by a setting unit by locating an additional pair of points defining a slab consisting of at least one slice to be scanned for the MR image.

3. The magnetic resonance imaging system of claim 2, further comprising a specifying unit configured to specify the number of slices composing a single slab serving as the sub-region to be imaged,
   wherein the setting unit is configured to set at least two slices adjacently and in parallel with each other on the basis of the located additional pair of points and the specified number of slices.

4. A magnetic resonance imaging system in which an object to be imaged is subjected to scanning to obtain an MR image, the scanning being applied to a sub-region of the object, the sub-region being previously located on a positioning image of the object, the system comprising:
   a displaying unit configured to display the positioning image;
   a locating unit configured to repetitively allow an operator to locate two points at desired points on the positioning image; and
   a setting unit configured to set the sub-region to be imaged substantially perpendicular to the positioning image on the basis of the located two points.

5. The magnetic resonance imaging system of claim 4, wherein the sub-region to be imaged set by the setting unit is a slab consisting of at least one slice to be scanned for obtaining the MR image.

6. The magnetic resonance imaging system of claim 5, further comprising a specifying unit configured to specify the number of slices composing a single slab serving as the sub-region to be imaged,
   wherein the setting unit is configured to set at least two slices adjacently and in parallel with each other on the basis of the located two points and the specified number of slices.

7. A method for planning a sub-region to be scanned by magnetic resonance imaging, the sub-region of the object being previously located on a positioning image previously acquired from the object, the method comprising:
   displaying the positioning image;
   interactively allowing two points to be located at desired points on the positioning image; and
   setting the sub-region to be imaged substantially perpendicular to the positioning image on the basis of the located two points.

8. A magnetic resonance imaging system in which an object to be imaged is subjected to scanning to obtain an MR image, the scanning being applied to a sub-region of the object to be imaged previously located on a positioning image of the object, the system comprising:
   displaying means for displaying the positioning image;
   locating means for interactively allowing an operator to locate two points at desired points on the positioning image; and
   setting means for setting a sub-region not to be imaged substantially perpendicular to the positioning image on the basis of the located two points, the sub-region not to be imaged being a saturation sub-region to be saturated with an MR signal before scanning for the MR image.

9. The magnetic resonance imaging system of claim 8, wherein the sub-region to be imaged is also set by a setting means by locating an additional pair of points defining a slab consisting of at least one slice to be scanned for obtaining the MR image.

10. The magnetic resonance imaging system of claim 9, further comprising specifying means for specifying the number of slices composing a single slab serving as the sub-region to be imaged,
   wherein the setting means is configured to set at least two slices adjacently and in parallel with each other on the basis of the additional pair of located points and the specified number of slices.

11. A magnetic resonance imaging system in which an object to be imaged is subjected to scanning to obtain an MR image, the scanning being applied to a sub-region of the object to be imaged, the sub-region to be imaged being previously located on a positioning image of the object, the system comprising:
   displaying means for displaying the positioning image;
   locating means for repetitively allowing an operator to locate each set of two points at desired points on the positioning image; and
   setting means for setting the sub-region to be imaged substantially perpendicular to the positioning image on the basis of the located two points.

12. The magnetic resonance imaging system of claim 11, wherein a sub-region to be imaged set by the setting means is a slab consisting of at least one slice to be scanned for obtaining the MR image.

13. The magnetic resonance imaging system of claim 12, further comprising specifying means for specifying the number of slices composing a single slab serving as the sub-region to be imaged,
   wherein the setting means is configured to set at least two slices adjacently and in parallel with each other on the basis of the located two points and the specified number of slices.

14. A method of locating a region to be scanned of an object to be imaged in magnetic resonance imaging, in which a sub-region of the object to be imaged is subjected to scanning to obtain an MR image thereof, the sub-region being previously located on a positioning image of the object, the method comprising:
   displaying the positioning image;
   interactively allowing an operator to locate two points at desired points on the positioning image; and
   setting a sub-region not to be imaged substantially perpendicular to the positioning image on the basis of the located two points, the sub-region not to be imaged being a saturation sub-region to be saturated with an MR signal before scanning the sub-region to be imaged for the MR image.

15. The method of claim 14, wherein sub-region to be imaged is also set by the setting step and includes a slab consisting of at least one slice to be scanned for obtaining the MR image.

16. The method of claim 15, further comprising specifying the number of slices composing a single slab serving as the sub-region to be imaged,
   wherein the setting step for a sub-regions to be imaged is configured to set at least two slices adjacently and in parallel with each other on the basis of the located two points and the specified number of slices.

17. A method of locating a region to be scanned of an object to be imaged by magnetic resonance imaging, in which a sub-region of the object to be imaged is subjected to scanning to obtain an MR image thereof, the sub-region to be imaged being previously located on a positioning image of the object, the method comprising:
   displaying the positioning image;
   repetitively allowing an operator to locate two points at desired points on the positioning image; and
   setting the sub-region to be imaged substantially perpendicular to the positioning image on the basis of the located two points.

18. The method of claim 17, wherein the sub-region to be imaged set by the setting step is a slab consisting of at least one slice to be scanned for obtaining the MR image.

19. The method of claim 18, further comprising specifying the number of slices composing a single slab serving as the sub-region to be imaged,
   wherein the setting step is configured to set at least two slices adjacently and in parallel with each other on the basis of the located two points and the specified number of slices.

* * * * *